United States Patent
Pearson et al.

(10) Patent No.: US 11,033,497 B2
(45) Date of Patent: Jun. 15, 2021

(54) (CITRIC) ACID/MALTODEXTRIN CO-AGGLOMERATE

(71) Applicant: The MBP Company LLC, Harrison, NY (US)

(72) Inventors: Matthew M. Pearson, Harrison, NY (US); William Valentine, Lawrenceville, GA (US); William K. Valentine, Lawrenceville, GA (US)

(73) Assignee: The MBP Company LLC, Harrison, NY (US)

( * ) Notice: Subject to any disclaimer, the term of this patent is extended or adjusted under 35 U.S.C. 154(b) by 42 days.

(21) Appl. No.: 15/685,708

(22) Filed: Aug. 24, 2017

(65) Prior Publication Data
US 2017/0348237 A1    Dec. 7, 2017

Related U.S. Application Data

(62) Division of application No. 14/338,854, filed on Jul. 23, 2014, now Pat. No. 9,820,944.

(60) Provisional application No. 61/857,464, filed on Jul. 23, 2013.

(51) Int. Cl.
| | |
|---|---|
| *A61K 9/16* | (2006.01) |
| *A23L 2/56* | (2006.01) |
| *A23L 2/39* | (2006.01) |
| *A23L 2/68* | (2006.01) |

(52) U.S. Cl.
CPC .............. *A61K 9/1652* (2013.01); *A23L 2/39* (2013.01); *A23L 2/56* (2013.01); *A23L 2/68* (2013.01); *A61K 9/1617* (2013.01); *A23V 2002/00* (2013.01)

(58) Field of Classification Search
CPC ....... A61K 9/1652; A61K 9/1617; A23L 2/56; A23L 2/39; A23V 2/00
See application file for complete search history.

(56) References Cited

U.S. PATENT DOCUMENTS

| | | | | |
|---|---|---|---|---|
| 4,684,534 | A | * 8/1987 | Valentine | ............ A61K 9/0056 264/4 |
| 4,704,269 | A | * 11/1987 | Korab | .................. A61K 9/0007 424/44 |
| 4,954,178 | A | 9/1990 | Caton | |
| 6,187,753 | B1 | 2/2001 | Noll et al. | |
| 6,365,182 | B1 | * 4/2002 | Khankari | ............ A61K 9/0007 424/466 |
| 6,579,535 | B2 | 6/2003 | Valentine et al. | |

* cited by examiner

*Primary Examiner* — Matthew P Coughlin
(74) *Attorney, Agent, or Firm* — DeLio Peterson & Curcio LLC; Keily M. Nowak

(57) ABSTRACT

Methods of making and resultant acidulent/carbohydrate agglomerates. The acidulent may be citric acid having particle sizes ranging from about 1 micron to 20 microns agglomerated with a soluble carbohydrate co-agglomerate to formulate the various acidulent/carbohydrate agglomerates. In certain embodiments, the carbohydrate co-agglomerate may be maltodextrin to formulate citric acid/maltodextrin agglomerates. These citric acid/maltodextrin agglomerates are shelf stable when dry, have improved flowability, compressibility, mixability; dissolve easily and quickly in water; and provide an easy ready-to-use formulation that is suitable for use in compounding various food and pharmaceutical products.

17 Claims, No Drawings

(CITRIC) ACID/MALTODEXTRIN CO-AGGLOMERATE

PRIORITY

This application is a divisional application of U.S. patent application Ser. No. 14/338,854 filed Jul. 23, 2014, which claims priority to U.S. Provisional Application Ser. No. 61/857,464 filed on Jul. 23, 2013, both of which are hereby incorporated by reference in their entireties.

BACKGROUND OF THE INVENTION

1) Field of the Invention

The present invention relates generally to water soluble agglomerates, and in particular, to water soluble maltodextrin and water soluble food grade acid agglomerate compositions.

2) Description of Related Art

In the food and pharmaceutical industries, a need has long existed for stable soluble acid agglomerates that rapidly dissolve in solution. Water soluble acid agglomerates are useful in the food industry in the formulation of powdered beverages, for example, in the formation of powdered lemonade. These soluble acid agglomerates are often mixed with other constituents of various particle sizes to formulate the desired food product mixture. In the pharmaceutical industry, soluble acid agglomerates are often useful in the formation of dispersible medicaments such as, for instance, water soluble ingestible medicines.

In order to ensure and enhance the rapid dissolution of soluble acid agglomerates it has been found that reducing the particle sizes of the acidulent to be dissolved is helpful to the dissolution thereof. However, in reducing the particle size of these soluble acid agglomerates, it has become more difficult to form stable dry blends. When reduced size soluble acid agglomerates are combined with different constituents of various particle sizes, the stability of such soluble acid agglomerates are often severely compromised. Further, when reduced size soluble acid agglomerates are combined or prepackaged with larger size particles, such a combination has deleterious effects on the soluble acid agglomerates' abilities to flow, compress, mix, and even their dissolution characteristics.

Accordingly, a need exists in the art for improved methods of making and reducing size soluble acid agglomerates, preferably water soluble acid agglomerates, that have improved stability, flow-ability, compress-ability, mix-ability, and dissolve readily in solution.

SUMMARY OF THE INVENTION

The aforementioned and other objects and advantages, which will be apparent to those skilled in the art, are achieved in the present invention which is directed to, agglomerated products that include acidulent binder agglomerate dispersed with a soluble carbohydrate agglomerate. These co-agglomerates formulate an acidulent/carbohydrate agglomerate.

In one or more embodiments, the acidulent may have particle sizes ranging from about 1 micron to 20 microns. The acidulent co-agglomerate may be citric acid such as, for example, granular citric acid, pulverized citric acid, or a 50% citric acid aqueous solution. The carbohydrate co-agglomerate may be maltodextrin. The acidulent/carbohydrate agglomerates of the invention may be used in food and/or pharmaceutical products.

The invention is also directed to agglomerated products that include a citric acid co-agglomerate binder having particle sizes ranging from about 1 micron to 20 microns agglomerated with and to soluble maltodextrin co-agglomerates. These products formulate citric acid/maltodextrin agglomerates that are honeycomb or zeolite-like structures with large voids and increased surface area. These citric acid/maltodextrin agglomerates may have densities ranging from about 0.28 g/cc to about 0.42 g/cc. In the various embodiments of the invention, the citric acid binder may be granular citric acid, pulverized citric acid, or a 50% citric acid aqueous solution.

Other embodiments of the invention are directed to methods of making the agglomerated products of the invention. In accordance with one or more embodiments, a bed load of carbohydrate co-agglomerate is provided within a chamber of an agglomerating device, followed by heating the chamber to energize such carbohydrate co-agglomerates. A predetermined amount of an acidulent co-agglomerating binder is also provided into the agglomerating device. The acidulent co-agglomerating binder is then atomized to provide reduced particle sizes of the acidulent binder. This reduced particle size acidulent binder is sprayed and dispersed with the bed load of carbohydrate co-agglomerates, followed by the drying thereof. The cycle of spraying, dispersing and drying are repeated until the acidulent co-agglomerating binder is depleted. Once depleted, the combined carbohydrate and acidulent co-agglomerates are dried to an entirely dry state to formulate the acidulent/carbohydrate agglomerates of the invention.

In the invention, the carbohydrate co-agglomerate may be a bed load of maltodextrin co-agglomeratate, while the acidulent co-agglomerating binder may be citric acid co-agglomerating binder. Further, the acidulent may be an acidulent co-agglomerating binder solution or it may be a dry acidulent co-agglomerating binder that is wetted during formation of the resultant acidulent/carbohydrate agglomerates. The carbohydrate co-agglomerate may be maltodextrin while the acidulent binder may be citric acid co-agglomerating binder to formulate a citric acid/maltodextrin agglomerate. These citric acid/maltodextrin agglomerates may have densities ranging from about 0.28 g/cc to about 0.42 g/cc. The final citric acid/maltodextrin agglomerate products may contain citric acid in a weight percentage of about 5.07% to about 20.00%.

DESCRIPTION OF THE PREFERRED EMBODIMENT(S)

The various embodiments of the invention are directed to reduced size soluble acid agglomerates that are permanently pre-dispersed within a soluble carbohydrate agglomerate. These acidulent/carbohydrate agglomerates are useful in food and pharmaceutical products because of their flowability, compressibility, mixability, stability and dissolution characteristics, among others. The acidulent/carbohydrate agglomerates of the invention store well, are convenient and pleasant to take, efficacious, fast acting and storage stable. The different embodiments of soluble acidulent/carbohydrate agglomerates of the invention dissolve easily and quickly in solution.

The soluble acidulent/carbohydrate agglomerates of the invention are broadly applicable to making a wide variety of food and pharmaceutical products including particulate blends and chewable tablets including but not limited to, tea and drink mixes (e.g., iced tea mixes, lemonade mixes, punch mixes, etc.), dissolvable medicines and/or chewable medicament tablets. Some of these powdered dissolvable and/or chewable tablets include, but are not limited to, antacids, cough medicine, sore throat, breath fresheners, vitamins, dietary supplements and nutrients, laxatives, cold tablets, analgesics, anti-diarrhea, reducing agents, pain relievers, sleeping aids, and many prescription and non-prescription drug and pharmaceutical tablets.

In accordance with the invention, the acidulent/carbohydrate agglomerates include an acidulent component in combination with a soluble carbohydrate component. The agglomerates of the invention are preferably water soluble that are stable in a dry blended state prior to use thereof. The various water soluble acidulent/carbohydrate agglomerates of the invention are provided in ready-to-use formulations that are suitable for use in compounding various food and pharmaceutical products as discussed above.

In the acidulent/carbohydrate agglomerates of the invention, the acidulent may be any food grade acid that can exist as a dry product, or is dry upon water removal. The acidulent component may be a food grade citric acid that is available as granular citric acid, pulverized citric acid, or as a 50% citric acid aqueous solution. In those embodiments that include the use of pulverized citric acid, it should be appreciated that pulverized citric acid is pharmacologically recognized as an artificial cough inducing agent. As such, adequate care, precautions and handling of pulverized citric acid should be taken to eliminate exposure to dust particles thereof (e.g., the use of dusk masks is advisable).

In accordance with the invention, it is preferred that the food grade citric acid be dry, or is able to be dried upon drying the instant acidulent/carbohydrate agglomerates. It is also preferred that the particle sizes of the food grade citric acid be reduced to assure rapid solubility and instant effectiveness for their intended purpose. In one or more embodiments, the acidulent component may comprise citric acid having reduced particle sizes ranging from above 0 microns to 30 microns, or more. Preferably the citric acid acidulent has particle sizes ranging from about 1 micron to 20 microns, or less.

In one or more embodiments the instant acidulent/carbohydrate based agglomerates are formulated using soluble food grade acidulent in an aqueous state. As such, any granular citric acid and/or pulverized citric acid used in formulating the agglomerate should be constituted, reconstituted or dissolved in solution. Preferably, the acidulent may be a food grade acidulent dissolved in water to serve as the agglomerate binder. This acidulent agglomerate binder is applied to the soluble carbohydrate component. In one or more embodiments the water soluble carbohydrate component may comprise maltodextrin.

Agglomerates according to the invention are preferably formed by a fluidized bed/agglomeration process in which the particles to be agglomerated are maintained in a gaseous suspension and the acidulent binder in a fine spray is applied to the suspended particles to cause them to adhere together and build into agglomerated particles. The resultant acidulent/carbohydrate agglomerates of the invention have honeycomb or zeolite like structures, with large amounts of voids or open pores that increase the surface area (i.e., they are porous, large surface area void-like structures). The various acidulent/carbohydrate based agglomerates for use in food and pharmaceutical preparations of the invention may be prepared using atomizing spray coaters that allow the acidulent binder constituent to be provided over a bed of the carbohydrate constituent.

In one or more embodiments, a suitable spray granulator for producing the acidulent/carbohydrate agglomerates of the invention may include a Freund Model FL 80 pilot-production Flow-Coater. A schematic diagram of the Freund Model FL 80 is depicted in FIGS. 1 and 2 of U.S. Pat. No. 4,684,534, which is hereby incorporated by reference in its entirety. While the Freund Model FL 80 may be used to formulate the instant agglomerates, it should be appreciated and understood that various other types of spray atomizers capable of providing coatings may be used to provide the present acidulent/carbohydrate based agglomerates. For instance, it has also been found that a Freund Mini-Flow-Coater is useful in providing results that can be replicated on production batch-type spray granulators. The Freund Mini-Flow-Coater includes a single, centrally-disposed nozzle that sprays atomized binder solution into a fluidized bed of the carbohydrate component. Other useful spray coaters also include those that provide continuous coatings (i.e., continuous agglomeration systems) for forming the instant acidulent/carbohydrate based agglomerates.

In accordance with one or more embodiments of the invention, the acidulent component acts as the binder or binding agent that may be used alone in solution, or optionally with the other active and/or inactive ingredients. When provided in a dry state, the acidulent component is used to prepare the binder solution. Alternatively, the acidulent may be as a prefabricated binder solution. The reduced size acidulent binder is typically applied in a mist-like or atomized spray having a droplet size of above 0 microns to 30 microns, or more, and preferably from about 1 micron to about 20 microns, onto the carbohydrate bed. The spray is preferably applied intermittently and the bed particles are dried between sprayings while they are continuously maintained suspended and in a fluidized state. Intermittent spray and drying continues until the required amount of binder solution has been sprayed into the bed. The moisture content of the bed is thereafter reduced preferably directly to the final desired moisture content or the equilibrium moisture content, and the agglomerated particles are removed from the bed and sized.

It is preferred that dried compressed air be used as the gas for atomizing the acidulent binder solution ("atomizing air"), as the gas for controlling the pattern of the spray ("spray pattern air"), and as the gas for suspending and fluidizing the particles in the body of the Flow-Coater. Other suitable gases may likewise be employed.

The air pressure of the atomizing air and pattern air and the pumping rate of the liquid binder solution are set and controlled in accordance with the particular agglomerate being produced as is well-known in the art. Also controlled are the quantity of fluidizing air being drawn to fluidize the bed particles, and the heat exchangers to set the temperature of the air introduced into the flow coater.

For the materials disclosed herein and similar materials, the atomizing air pressure and the pattern air pressure is typically (for equipment the size of the Freund FL80 Flow-Coater) in the general range of about 1.5 kg/cm$^2$ to about 6 kg/cm$^2$, the atomizing air flow in the general range of about 100 L/minute to about 200 L/minute, the pattern air flow in the general range of about 10 L/minute to about 40 L/minute, and the liquid binder flow rate in the general range of about 60 ml/minute to about 1,200 ml/minute. The following are preferred: atomizing air pressure and pattern air pressure, 1-4 kg/cm (i.e., 1-4 ATM); atomizing air flow of 170

L/minute; pattern air flow of 20 L/minute; and, liquid binder flow rate of 400 ml/minute. The fluidizing air temperatures may range from about 60-85° C., or more or less depending upon processing and atmospheric conditions.

The different process parameters described herein can be set and individually controlled by visual observation and manual setting, or by control systems which semi-automatically or automatically sense and regulate the parameters in accordance with a given control sequence. Process parameters for a particular agglomerate can be programmed into or manually set in to such control system. Computerized control systems can be used, if desired, and the construction and operation of control systems for controlling the foregoing process are within the skill of those in the computer and control system arts.

Examples of acidulent/carbohydrate agglomerates made in accordance with the described invention follow. While the examples show different embodiments of the invention, it should be appreciated and understood that these examples are not meant to limit the invention in any manner. Rather, such examples are intended to be exemplary and are not intended to be exhaustive or limiting. It should be appreciated that the invention is directed to numerous variants of these examples, all of which provide methods of making and the resultant acidulent/carbohydrate agglomerates made in accordance with the numerous embodiments encompassed by the description of the invention herein.

Acidulent/carbohydrate agglomerates of the invention, as shown in the examples below, were made in accordance with processes described herein using a Freund Mini-Flow-Coater. The agglomerates were made from materials as indicated herein with citric acid as the acidulent binding agglomerating component and maltodextrin as the carbohydrate agglomerating component. In these examples, the maltodextrin used is a product of Grain Processing Corporation (GPC), Muscatine, Iowa. The citric acid used is a product of Tate and Lyle (T&L), Decatur, Ill. In those examples implementing a prefabricated acidulent binder solution, such solution comprises a citric acid solution (50% w/w) having a citric acid content of 0.62 g/cc. The effective amount quantity of this 50% aqueous citric acid binder solution varies depending on the desired acidulent/carbohydrate agglomerate end-product in accordance with the invention.

Again, the resultant acidulent/carbohydrate agglomerates made in accordance with the invention have honeycomb or zeolite-like structures with large amounts of voids and surface area. The instant agglomerates are a stable blend of water soluble carbohydrate/acidulent co-agglomerates that reduce the number of materials in product inventory. The resultant acidulent/carbohydrate agglomerates may be compressed into tablets having desired agglomerate particle sizes depending upon the desired usage of such agglomerates.

EXAMPLES: The following examples serve to further illustrate the components and details of preparation for the reduced size acidulent based co-agglomerate binder spray, preferably sprayed in solution at particle sizes of 20 microns or less, onto the carbohydrate co-agglomerate bed to formulate the various acidulent/carbohydrate agglomerates of the invention. The following examples were performed and made using a Freund Mini Flow-Coater.

Example 1

A bench model Freund Mini Flow-Coater fluid bed agglomerator product bowl was charged with a bed load comprising 360 g powdered maltodextrin (Maltrin M-100, GPC). The bed of powdered maltodextrin was energized and preheated with inlet air at a temperature of 80° C. for a period of about 5 minutes.

An agglomerating pump solution was prepared by providing a pump solution of 70 ml citric acid solution (50% w/w, T&L). The pump was energized at a rate of 2 ml/minute, and the citric acid solution was delivered as an atomized spray through the use of compressed air delivered to the single spray nozzle at a pressure of 1.0 kg/cm$^2$ (i.e., 1.0 ATM). At the end of each 4 cycles of spray, the bed was dried for a period of about 4 minutes before spraying continued. This pattern was followed until the entire amount of the spray solution (70 ml) was delivered.

At the end of the spray and sub-dry cycles, the product was then finally dried to a loss on drying (LOD) moisture content of about 6.0%; Density of 0.32 g/cc; and Citric acid content of 10.76%. The finished acidulent/carbohydrate agglomerate product was shelf stable; had improved flowability, compressibility, mixability; dissolved easily and quickly in water; and provide an easy ready-to-use formulation that is suitable for use in compounding various food and pharmaceutical products as discussed above.

Example 2

A bench model Freund Mini Flow-Coater fluid bed agglomerator product bowl was charged with a bed load comprising 360 g powdered maltodextrin (Maltrin M-100, GPC), and an agglomerating binder comprising 40 g milled, powdered citric acid (T&L). The bed of powdered maltodextrin and citric acid was energized and preheated with inlet air at a temperature of 80° C. for a period of about 5 minutes.

A pump solution of water was energized at a rate of 2 ml/minute, and the water was delivered as an atomized spray through the use of compressed air delivered to the single spray nozzle at a pressure of 1.0 kg/cm$^2$ (i.e., 1.0 ATM). At the end of each 4 cycles of spray, the bed was dried for a period of about 4 minutes before spraying continued. This pattern was followed until a sufficient amount of water was delivered.

At the end of the spray and sub-dry cycles, the product was finally dried to a loss on drying (LOD) moisture content of about 5.9%; Density of 0.36 g/cc; and Citric acid content of 10.00%. The finished acidulent/carbohydrate agglomerate product was shelf stable; had improved flowability, compressibility, mixability; dissolved easily and quickly in water; and provide an easy ready-to-use formulation that is suitable for use in compounding various food and pharmaceutical products as discussed above.

Example 3

A bench model Freund Mini Flow-Coater fluid bed agglomerator product bowl was charged with a bed load comprising 360 g powdered maltodextrin (Maltrin M-100, GPC). The bed of powdered maltodextrin was energized and preheated with inlet air at a temperature of 80° C. for a period of about 5 minutes.

An agglomerating pump solution was prepared by providing a pump solution of 80 ml citric acid solution (50% w/w, T&L). The pump was energized at a rate of 2 ml/minute, and the citric acid solution was delivered as an atomized spray through the use of compressed air delivered to the single spray nozzle at a pressure of 1.0 kg/cm$^2$ (i.e., 1.0 ATM). At the end of each 4 cycles of spray, the bed was dried for a period of about 4 minutes before spraying continued. This pattern was followed until the entire amount of the spray solution (80 ml) was delivered.

At the end of the spray and sub-dry cycles, the product was then finally dried to a loss on drying (LOD) moisture content of about 6.3%; Density of 0.42 g/cc; and Citric acid content of 12.11%. The finished acidulent/carbohydrate agglomerate product was shelf stable; had improved flowability, compressibility, mixability; dissolved easily and quickly in water; and provide an easy ready-to-use formulation that is suitable for use in compounding various food and pharmaceutical products as discussed above.

Example 4

A bench model Freund Mini Flow-Coater fluid bed agglomerator product bowl was charged with a bed load comprising 360 g powdered maltodextrin (Maltrin M-100, GPC). The bed of powdered maltodextrin was energized and preheated with inlet air at a temperature of 80° C. for a period of about 5 minutes.

An agglomerating pump solution was prepared by providing a pump solution of 120 ml citric acid solution (50% w/w, T&L). The pump was energized at a rate of 2 ml/minute, and the citric acid solution was delivered as an atomized spray through the use of compressed air delivered to the single spray nozzle at a pressure of 1.0 kg/cm$^2$ (i.e., 1.0 ATM). At the end of each 4 cycles of spray, the bed was dried for a period of about 4 minutes before spraying continued. This pattern was followed until the entire amount of the spray solution (120 ml) was delivered.

At the end of the spray and sub-dry cycles, the product was then finally dried to a loss on drying (LOD) moisture content of about 6.1%; Density of 0.38 g/cc; and Citric acid content of 17.13%. The finished acidulent/carbohydrate agglomerate product was shelf stable; had improved flowability, compressibility, mixability; dissolved easily and quickly in water; and provide an easy ready-to-use formulation that is suitable for use in compounding various food and pharmaceutical products as discussed above.

Example 5

The experiment of Example 4 above was repeated in this Example; however, an agglomerating pump solution was prepared by providing a pump solution of 150 ml citric acid solution (50% w/w, T&L). The processing conditions were the same as those in Example 4, and repeated until the entire amount of the spray solution (150 ml) was delivered.

At the end of the spray and sub-dry cycles, the product was then finally dried to a loss on drying (LOD) moisture content of about 6.9%; Density of 0.40 g/cc; and Citric acid content of 20.53%. The finished acidulent/carbohydrate agglomerate product had the same properties as discussed above in relation to the other examples described herein.

Example 6

The experiment of Example 4 and 5 was repeated in this Example; however, an agglomerating pump solution was prepared by providing a pump solution of 31 ml citric acid solution (50% w/w, T&L). The processing conditions were the same as those in Example 4, and repeated until the entire amount of the spray solution (31 ml) was delivered.

At the end of the spray and sub-dry cycles, the product was then finally dried to a loss on drying (LOD) moisture content of about 8.3%; Density of 0.28 g/cc; and Citric acid content of 5.07%. The finished acidulent/carbohydrate agglomerate product had the same properties as discussed above in relation to the other examples described herein.

Example 7

A bench model Freund Mini Flow-Coater fluid bed agglomerator product bowl was charged with a bed load comprising 320 g powdered maltodextrin (Maltrin M-100, GPC), and an agglomerating binder comprising 80 g screened, powdered citric acid (T&L). The bed of powdered maltodextrin and citric acid was energized and preheated with inlet air at a temperature of 80° C. for a period of about 5 minutes.

A pump solution of water was energized at a rate of 2 ml/minute, and the water was delivered as an atomized spray through the use of compressed air delivered to the single the bed was dried for a period of about 4 minutes before spraying continued. This pattern was followed until a sufficient amount of water was delivered.

At the end of the spray and sub-dry cycles, the product was finally dried to a loss on drying (LOD) moisture content of about 6.6%; Density of 0.40 g/cc; and Citric acid content of 20.00%. The finished acidulent/carbohydrate agglomerate product was shelf stable; had improved flowability, compressibility, mixability; dissolved easily and quickly in water; and provided an easy ready-to-use formulation that is suitable for use in compounding various food and pharmaceutical products as discussed above.

Example 8

It should be appreciated that different processing parameters may also be used in formulating the acidulent/carbohydrate agglomerates of the invention having the above discussed properties. In Example 8, a bed load of 360 g powdered maltodextrin (Maltrin M-100, Grain Processing) and 65 ml citric acid solution (50% w/w, T&L) were provided in a bench model Freund Mini Flow-Coater fluid bed agglomerator.

The bed of powdered maltodextrin was energized and preheated with inlet air at a temperature of 70° C. for a period of about 5 minutes. The pump was energized at a rate of 2 ml/minute, and the citric acid solution was delivered as an atomized spray through the use of compressed air delivered to the single spray nozzle at a pressure of 3.5 kg/cm$^2$ (i.e., 3.5 ATM). At the end of each 4 cycles of spray, the bed was dried for a period of about 4 minutes before spraying continued. This pattern was followed until the entire amount of the spray solution (65 ml) was delivered. At the end of the spray and sub-dry cycles, the product was then finally dried to a loss on drying (LOD) moisture content of about 6.0%; Density of 0.32 g/cc; and Citric acid content of 10.00%.

Example 9

While the above Examples each employ the use of maltodextrin in the form of Maltrin M-100 as the carbohydrate agglomerating component, it should be appreciated that other forms of maltodextrin may also be used in the invention. In this example, a Freund Mini Flow-Coater fluid bed agglomerator product bowl was charged with a bed load of 360 g maltodextrin in the form of Maltrin M-500, GPC.

The bed of powdered Maltrin M-500 maltodextrin was energized and preheated with inlet air at a temperature of 70° C. for a period of about 5 minutes. The pump was energized at a rate of 2 ml/minute, and a citric acid solution of 65 ml citric acid solution (50% w/w, T&L) was delivered as an atomized spray through the use of compressed air delivered to the single spray nozzle at a pressure of 3.5 kg/cm² (i.e., 3.5 ATM). The bed was sprayed and dried for a number of cycles, and repeated until the 65 ml spray solution was delivered. Upon final dry, the product was dried to a loss on drying (LOD) moisture content of about 6.2%.

Examples 10 and 11

The above Examples 1-9 were described in relation to formulating the acidulent/carbohydrate agglomerates of the invention in small batches using a Freund Mini Flow-Coater fluid bed agglomerator. It should be appreciated that larger batches of the instant acidulent/carbohydrate agglomerates may also be formulated. In these examples a Freund Model FL-80 Pilot-Production Flow-Coater fluid bed agglomerator was implemented to formulate large amounts of the instant acidulent/carbohydrate agglomerates.

In Example 10, Freund Model FL-80 Pilot-Production Flow-Coater was charged with a bed load comprising 45 kg powdered maltodextrin (Maltrin M-100, GPC). An agglomerating pump solution of 8 L citric acid solution (50% w/w, T&L) was charged into an agitated holding tank. Prior to energizing the machine, the following operational parameters for the agglomeration of the fluidized bed were set into the operational computer: an inlet air temperature of 75° C.; atomizing air pressure of 4.0 kg/cm² (i.e., 4.0 ATM); pump delivery rate of 400 ml/min; filter shake interval of 15 seconds; number of pump/shake cycles of 20; atomizing air to spray guns of 170 L/min; pattern air to spray guns of 20 L/min; a bed mixing time of about 5 min.; and a sub-dry after each 5 pump cycles of about 5 min.

The above parameters were set into the electronic control system of the FL-80, and the FL-80 agglomerating machine was energized based on the above parameters so that fluidization of the bed was effected in accordance with the invention. After each minute of time in the agglomeration cycle, fluidization was interrupted and the filters were automatically shaken followed by re-established fluidization. The spray/shake cycles continued until all of the pump atomizing solution plus system flush water was delivered onto the bed. The agglomerated bed was then dried by fluidization in the heated inlet air until a final moisture of 6.3% (LOD) was reached.

In Example 11, the Freund Model FL-80 Pilot-Production Flow-Coater was charged with a bed load comprising 45 kg powdered maltodextrin (Maltrin M-500, GPC), with 8 L citric acid solution (50% w/w, T&L) of agglomerating pump solution in the agitated holding tank. This example was performed under the processing conditions set forth in Example 10, and at the end of the spray and sub-dry cycles, the product was finally dried to a loss on drying (LOD) moisture content of about 6.2%.

In accordance with the different embodiments and examples described herein, each finished acidulent/carbohydrate agglomerate product of the invention is shelf stable; has improved flowability, compressibility, mixability; dissolves easily and quickly in water; and provides an easy ready-to-use formulation that is suitable for use in compounding various food and pharmaceutical products as discussed above.

While the present invention has been particularly described it is evident that many alternatives, modifications, and variations will be apparent to those skilled in the art in the light of the forgoing description. It is therefore contemplated that the appended claims will embrace any such alternatives, modifications and variations as falling within the true scope and spirit of the present invention.

Thus, having described the invention, what is claimed is:

1. An agglomerated product consisting of a citric acid binder dispersed within and agglomerated to soluble maltodextrin to form a citric acid/maltodextrin agglomerate product having a moisture content ranging from about 5.9% to about 8.3%, a density ranging from about 0.28 g/cc to about 0.42 g/cc, and a citric acid content in a weight percentage ranging from about 5.07% to about 20.53%, the citric acid/maltodextrin agglomerate product formulated in a heated agglomerator device having a temperature ranging from 60° C. to 85° C. by atomizing the citric acid binder and spraying the atomized citric acid binder having particle sizes ranging from 1 micron to less than 20 microns onto an energized bed of soluble maltodextrin preheated at said temperature ranging from 60° C. to 85° C.

2. The product of claim 1 wherein the citric acid binder is a 50% citric acid aqueous solution.

3. The product of claim 1 wherein the citric acid/maltodextrin agglomerate resides in a food product.

4. The product of claim 1 wherein the citric acid/maltodextrin agglomerate resides in a pharmaceutical product.

5. The product of claim 1 wherein the citric acid binder is granular citric acid in solution or pulverized citric acid in solution, said citric acid/maltodextrin agglomerate having honeycomb or zeolite-like structures.

6. An agglomerated product consisting essentially of:
a citric acid/maltodextrin agglomerate product formulated from a citric acid binder dispersed within soluble maltodextrin and having a citric acid content in weight percentage ranging from about 5.07% to about 20.53%, the citric acid/maltodextrin agglomerate product formulated in a heated agglomerator device having a temperature ranging from 60° C. to 85° C. by atomizing the citric acid binder, and spraying and dispersing the atomized citric acid binder having particle sizes ranging from 1 micron to less than 20 microns onto an energized, heated bed load of soluble maltodextrin maintained in a gaseous suspension and preheated at said temperature ranging from 60° C. to 85° C., said spraying and dispersing repeating for a number of repeated cycles until the citric acid binder is depleted to formulate the citric acid/maltodextrin agglomerate product having honeycomb or zeolite-like structures.

7. The product of claim 6 wherein the citric acid binder is granular citric acid in solution.

8. The product of claim 6 wherein the citric acid binder is pulverized citric acid in solution.

9. The product of claim 6 wherein the citric acid binder is a 50% citric acid aqueous solution.

10. The product of claim 6 wherein the citric acid/maltodextrin agglomerate has a moisture content ranging from about 5.9% to about 8.3%, and a density ranging from about 0.28 g/cc to about 0.42 g/cc.

11. The product of claim 6 further including one or more additional ingredient in combination with the citric acid binder.

12. The product of claim 6 wherein the citric acid/maltodextrin agglomerate contains citric acid in a weight percentage of about 5.07% to about 20.00%.

13. The product of claim 6 wherein the citric acid/maltodextrin agglomerate resides in a food product or a pharmaceutical product.

14. An acidulent/carbohydrate agglomerated product consisting essentially of:
a citric acid/maltodextrin agglomerate product having a citric acid content in a weight percentage ranging from about 5.07% to about 20.53%, whereby atomized citric acid binder and soluble maltodextrin are used to form the citric acid/maltodextrin agglomerate product by;
providing a bed load of the soluble maltodextrin co-agglomerate within a chamber of an agglomerator device;
heating said chamber to a temperature ranging from 60° C. to 85° C. to energize the bed load of soluble maltodextrin co-agglomerate;
providing a predetermined amount of citric acid binder into the agglomerator device;
atomizing the citric acid binder to provide the atomized citric acid binder having reduced particle sizes ranging from 1 micron to less than 20 microns;
spraying and dispersing the atomized citric acid binder onto the energized, heated bed load of soluble maltodextrin co-agglomerate, followed by drying said soluble maltodextrin co-agglomerate and citric acid binder;
repeating the spraying, dispersing and drying cycles until the citric acid binder is depleted; and
once the citric acid binder is depleted, drying said soluble maltodextrin co-agglomerate and citric acid binder to a dry state to formulate the citric acid/maltodextrin agglomerate.

15. The product of claim 14 wherein the citric acid/maltodextrin agglomerate has a moisture content ranging from about 5.9% to about 8.3%, and a density ranging from about 0.28 g/cc to about 0.42 g/cc.

16. The product of claim 14 wherein the citric acid binder is a 50% citric acid binder solution, the citric acid/maltodextrin agglomerate is formulated within the agglomerator device under processing conditions comprising;
atomizing air pressure ranging from 1.5 $kg/cm^2$ to 6 $kg/cm^2$,
atomizing air flow ranging from 100 L/minute to 200 L/minute,
pattern air flow ranging from 10 L/minute to 40 L/minute, and
binder solution flow rate ranging from 60 ml/minute to 1,200 ml/minute.

17. The product of claim 14 wherein the citric acid binder is a 50% citric acid binder solution, the citric acid/maltodextrin agglomerate is formulated within the agglomerator device under processing conditions comprising;
atomizing air pressure of 1 $kg/cm^2$ to 4 $kg/cm^2$,
pattern air flow of 20 L/minute,
binder solution flow rate of 400 ml/minute, and
said temperature ranging from 70° C. to 80°.

* * * * *

UNITED STATES PATENT AND TRADEMARK OFFICE
CERTIFICATE OF CORRECTION

PATENT NO. : 11,033,497 B2
APPLICATION NO. : 15/685708
DATED : June 15, 2021
INVENTOR(S) : Matthew M. Pearson, William Valentine and William K. Valentine Page 1 of 1

It is certified that error appears in the above-identified patent and that said Letters Patent is hereby corrected as shown below:

In the Specification

Column 8, Line 17, delete "single the bed was dried for a period of about 4 minutes before spraying continued." and substitute therefor "single spray nozzle at a pressure of 1.0 kg/cm$^2$ (i.e., 1.0 ATM). At the end of each 4 cycles of spray, the bed was dried for a period of about 4 minutes before spraying continued."

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*